US00PP28111P3

(12) United States Plant Patent
O'Connell

(10) Patent No.: US PP28,111 P3
(45) Date of Patent: Jun. 13, 2017

(54) ***CRASSULA* PLANT NAMED 'CANDY CANE'**

(50) Latin Name: *Crassula rubricaulis*
Varietal Denomination: Candy Cane

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 82 days.

(21) Appl. No.: 14/544,919

(22) Filed: Mar. 6, 2015

(65) Prior Publication Data

US 2016/0270284 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Crassula* cultivar named 'Candy Cane' is disclosed, characterized by an unusual, stable, tricolor variegation, comprised of white leaves, with marbling of mint green, accented by rose magenta margins. In addition, the new cultivar 'Candy Cane' branches as a young plant, and continues to rapidly branch, producing many terminal vegetative cuts that greatly enhance propagation of the cultivar in the commercial nursery. Additionally, the prolific branching quickly produces an attractive, fully branched that readily fills the production container, resulting in plants ready for sale at an earlier size, thereby reducing production times in the commercial nursery. The new variety is a *Crassula*, part of the Crassulaceae complex that includes *Crassula, Crassula, Pachyphytum, Graptopelalum, Sedum* and others. *Crassula* is a popular genus, typically produced as container plants or as landscape plants.

2 Drawing Sheets

Figure 1:
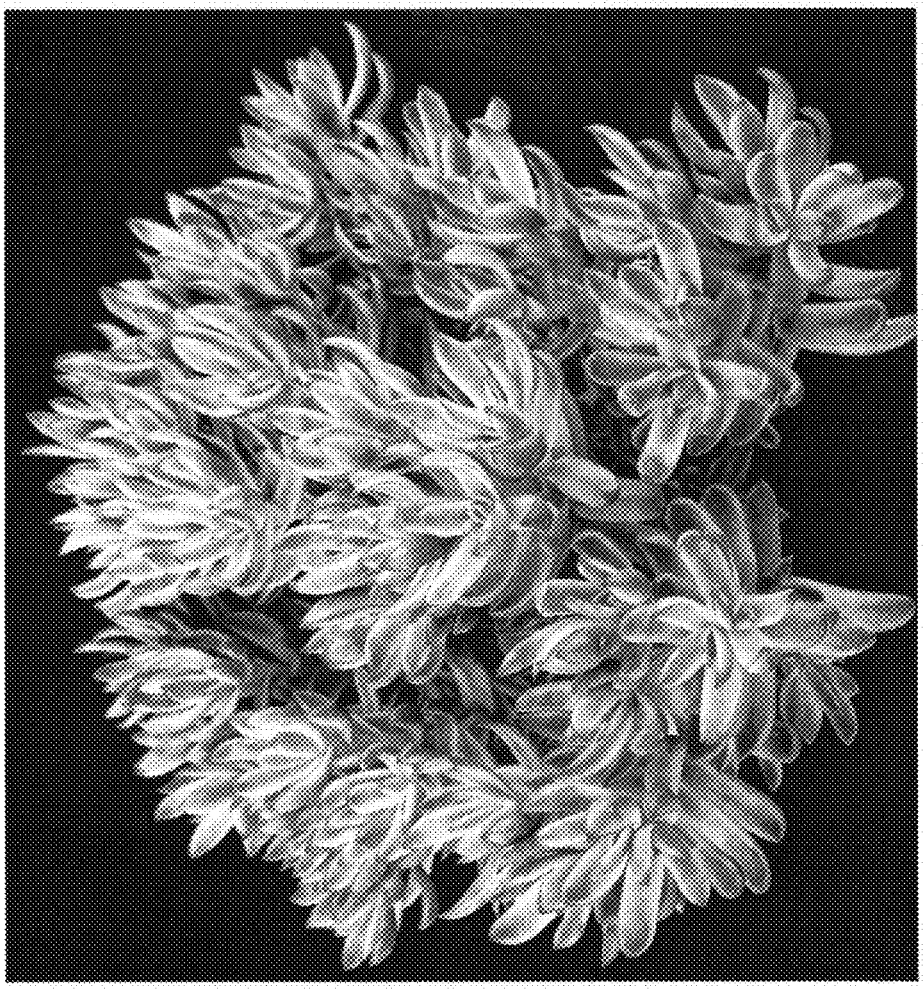

Latin name of the genus and species: *Crassula rubricaulis.*

Variety denomination: 'CANDY CANE'.

BACKGROUND OF THE INVENTION

The new cultivar, *Crassula* 'Candy Cane', was found in an existing population of propagation stock plants of *Crassula rubricaulis* in a commercial greenhouse in Vista, Calif. by the inventor, Renee O'Connell. *Crassula* 'Candy Cane' is a naturally occurring branch mutation of an unknown *Crassula rubricaulis*. The new cultivar, *Crassula* 'Candy Cane' was discovered by the inventor, Renee O'Connell, in December of 2012

Asexual reproduction of the new cultivar 'Candy Cane' was first performed in Vista, Calif., at a commercial greenhouse, by vegetative cuttings in February of 2013. 'Candy Cane' has since produced multiple generations and has shown that the unique features of this cultivar are stable and reproduced true to type.

SUMMARY OF THE INVENTION

The cultivar 'CANDY CANE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CANDY CANE' These characteristics in combination distinguish 'CANDY CANE' as a new and distinct *Crassula* cultivar:

1. Displays an unusual variegation of the leaves; consisting of white leaves, with some marbling of mint green, accented by magenta rose margins, not displayed by other comparable *Crassula* varieties.
2. Exhibits a stable variegation, not shown by many comparable *Crassula* varieties.
3. Easily and rapidly propagated due to prolific branching, producing many terminal vegetative cuttings, compared to many other *Crassula* cultivars.
4. Branches prolifically, allowing for shorter production intervals as compared with many other *Crassula* cultivars.

Plants of the new cultivar 'CANDY CANE' are similar to plants of the seed parent, *Crassula rubricaulis* in most horticultural characteristics, however, plants of the new cultivar 'CANDY CANE' differ in the following;

1. Grows with a more compact morphology than *Crassula rubricaulis*, enabling use for smaller pot sizes, such as 6 cm and 9 cm.
2. Displays an unusual tricolor variegation, comprised of predominately white leaves with areas of mint green, accented by rose magenta margins, whereas *Crassula rubricaulis* does not display this variegation.

COMMERCIAL COMPARISON

Plants of the new cultivar 'CANDY CANE' are comparable to the unpatented, commercial variety *Crassula capitella* 'Campfire'. The two *Crassula* varieties are similar in most horticultural characteristics; however, the new variety 'CANDY CANE' differs in the following:

1. Exhibits a stable variegation, whereas *Crassula capitella* 'Campfire' exhibits a very unstable variegation, often reverting to non-variegated growth.
2. Branches profusely, forming a much-branched shrublet, in contrast to *Crassula capitella* 'Campfire' which branches much less.
3. Displays a more compact, precise growth habit, whereas *Crassula capitella* 'Campfire' grows with a sprawling habit.
4. Branches profusely, enabling much faster propagation and production.
5. Does not suffer the same interruption of propagation that *Crassula capitella* 'Campfire' does due to intermittent flowering during the late summer months.

Plants of the new cultivar 'CANDY CANE' can also be comparable to the unpatented commercial variety *Crassula pellucida* ssp. *marginalis* 'Variegata'. The two *Crassula* varieties are similar in most horticultural characteristics; however, the new variety 'CANDY CANE' differs in the following:

1. Exhibits a stable variegation, whereas *Crassula pellucida* ssp. *marginalis* 'Variegata' readily reverts, and loses its variegation.
2. Grows with an upright, branching morphology, in contrast to *Crassula pellucida* ssp. *marginalis* 'Variegata', which grows with a prostrate morphology.

BRIEF DESCRIPTION OF THE PHOTOGRAPHS

The accompanying photograph in FIG. 1 illustrates in full color the new *Crassula* plant 'Candy Cane' as grown in a commercial greenhouse in Vista, Calif.

Figure 2:
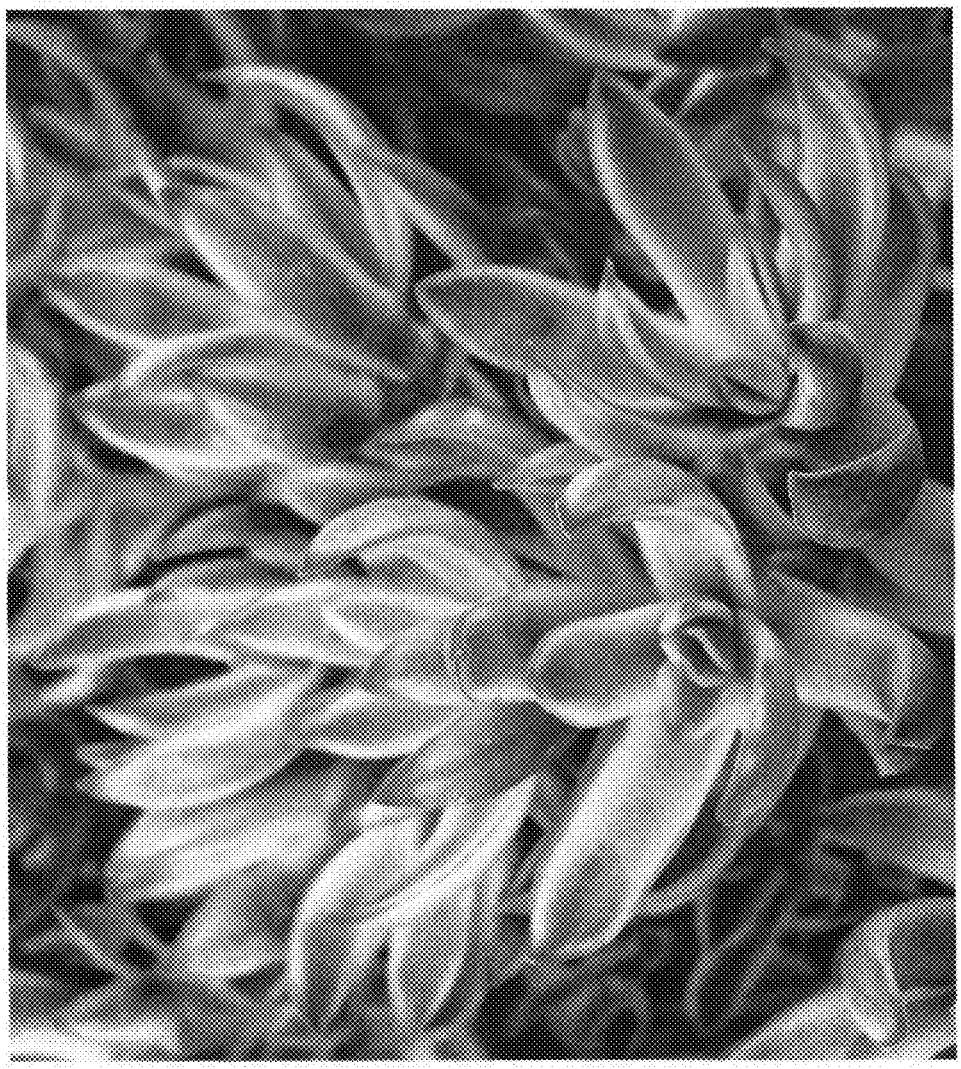

FIG. 2 illustrates a close-up of the variegation of the new *Crassula* plant 'Candy Cane' as grown in a commercial greenhouse in Vista, Calif. Age of the plant photographed is approximately 14 weeks from a well rooted cutting.

The photographs were taken using conventional techniques and although colors may appear different from actual colors due to light reflectance it is as accurate as possible by conventional photographic techniques. All photographs provided by breeder.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Candy Cane' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Crassula rubricaulis* 'CANDY CANE'.

PROPAGATION

Type of propagation typically used: Terminal vegetative divisions.

Time to initiate roots: About 16 days at approximately 25° C.

Root description: Fibrous.

PLANT

Age of plant described: Approximately 10 months.

Container size of the plant described: 16 cm.

Growth habit: Much branched shrublet.

Height: Approximately 22 cm to top of highest leaf. Height in cm to top of inflorescence is unknown as plant has been undergoing propagation, and has not yet flowered.

Plant spread: Approximately 21 cm.

Growth rate: Moderately fast.

Branching characteristics: Frequently branching.

FOLIAGE

Leaf:

*Arrangement*.—Opposite decussate.

*Average length*.—Approximately 3.2 cm.

*Longest length*.—Approximately 3.8 cm.

*Widest width*.—Approximately 1.1 cm.

*Width at base*.—0.95 cm.

*Shape of blade*.—Oblanceolate-cultrate.

*Apex*.—Acute.

*Base*.—Clasping.

*Margin*.—Ciliate.

*Texture of top surface*.—Glabrous.

*Texture of bottom surface*.—Glabrous.

*Quantity of leaves per plant*.—Approximately 1052. (9 major sterns, heavily ramified).

*Color*.—Young foliage upper side, middle of leaf: Near P 1-2 U Pantone. Young foliage, upper side, margin: Near P 71-7 U Pantone (light color). Young foliage upper side, green apical and basal area, striations: Near P 132-11 U Pantone. Young foliage, under side: Near P 132-11 U Pantone (green color). Young foliage, under side, margin: Near P 71-14 U Pantone. Young foliage, under side, area near margin: Near P 132-1 U Pantone. Mature foliage, upper side: Near P 159-1 U Pantone (light color). Mature foliage, upper side: Near P 135-12 U Pantone (green color; apex, midstripe, base and striations). Mature foliage, upper side, margin: Near P 69-2 U Pantone. Mature foliage under side: Near P 137-1 U Pantone. Mature foliage, under side, striations & islands: Near P 135-3 U Pantone. Mature foliage, under side, margin: Near P 74-5 U Pantone.

*Venation*.—There is no visual appearance of venation.

FLOWER

Flowering not observed to date.

REPRODUCTIVE ORGANS

Unknown, flower has not yet been observed.

OTHER CHARACTERISTICS

Fruits and seeds: Unknown; has not flowered to date.

Temperature tolerance: Tolerates temperatures from approximately −2 C to 32 C.

Disease/pest resistance: No increased nor decreased resistance to normal diseases and pests of *Crassula* has been observed.

Drought tolerance: Tolerates at least 3 weeks of high temperatures without supplemental water, showing no serious damage to plant.

What is claimed is:

1. A new and distinct cultivar of *Crassula* plant named 'CANDY CANE' as herein illustrated and described.

* * * * *